（12）United States Patent
Czege et al.

(10) Patent No.: US 7,773,219 B2
(45) Date of Patent: Aug. 10, 2010

(54) PROCESS AND APPARATUS FOR MEASUREMENTS OF MUELLER MATRIX PARAMETERS OF POLARIZED LIGHT SCATTERING

(75) Inventors: Jozsef Czege, Highland, MD (US); Burt V. Bronk, Abington, MD (US)

(73) Assignee: The United States of America as represented by the Secretary of the Air Force, Wright-Patterson Air Force Base, OH (US)

( * ) Notice: Subject to any disclaimer, the term of this patent is extended or adjusted under 35 U.S.C. 154(b) by 121 days.

(21) Appl. No.: 12/082,195

(22) Filed: Mar. 31, 2008

(65) Prior Publication Data

US 2009/0033938 A1 Feb. 5, 2009

Related U.S. Application Data

(63) Continuation of application No. PCT/US2006/038463, filed on Oct. 3, 2006.

(60) Provisional application No. 60/722,405, filed on Oct. 3, 2005.

(51) Int. Cl.
*G01J 4/00* (2006.01)
(52) U.S. Cl. .................................. 356/364; 356/368
(58) Field of Classification Search .......... 356/364–369
See application file for complete search history.

(56) References Cited

U.S. PATENT DOCUMENTS

| 4,884,886 | A | 12/1989 | Salzman et al. |
| 6,011,626 | A | 1/2000 | Hielscher et al. |
| 6,060,710 | A | 5/2000 | Carrieri et al. |
| 6,721,051 | B2 | 4/2004 | Mengüç et al. |
| 6,738,137 | B2 * | 5/2004 | Oakberg ............... 356/365 |

OTHER PUBLICATIONS

Van De Merwe et al, Rapid optically based measurements of diameter and length for spherical or rod-shaped bacteria in vivo, Oct. 2004, Applied Physics, vol. 43, N. 28.*
M. Myrick, "*University of South Carolina CB Support, Basic Research in Materials and Techniques for Optical Computing Stand-off Sensors*", Technical Report AFRL-HE-WP-TR-2004-0149, Oct. 2004, pp. 1-74.

* cited by examiner

*Primary Examiner*—L. G Lauchman
(74) *Attorney, Agent, or Firm*—AFMCLO/JAZ; Christopher J. Menke; Jeffrey R. Moore

(57) ABSTRACT

A method and apparatus for measuring Mueller matrix parameters from scattered light. The apparatus is advantageous for use in countering bioterrorism by detecting information concerning airborne pathogens, particularly microorganism in aerosol form. The system provided is portable, more efficient, and less sensitive to wavelength changes. The method uses variation in retardation over wavelength as opposed to variation in retardation with time.

13 Claims, 18 Drawing Sheets

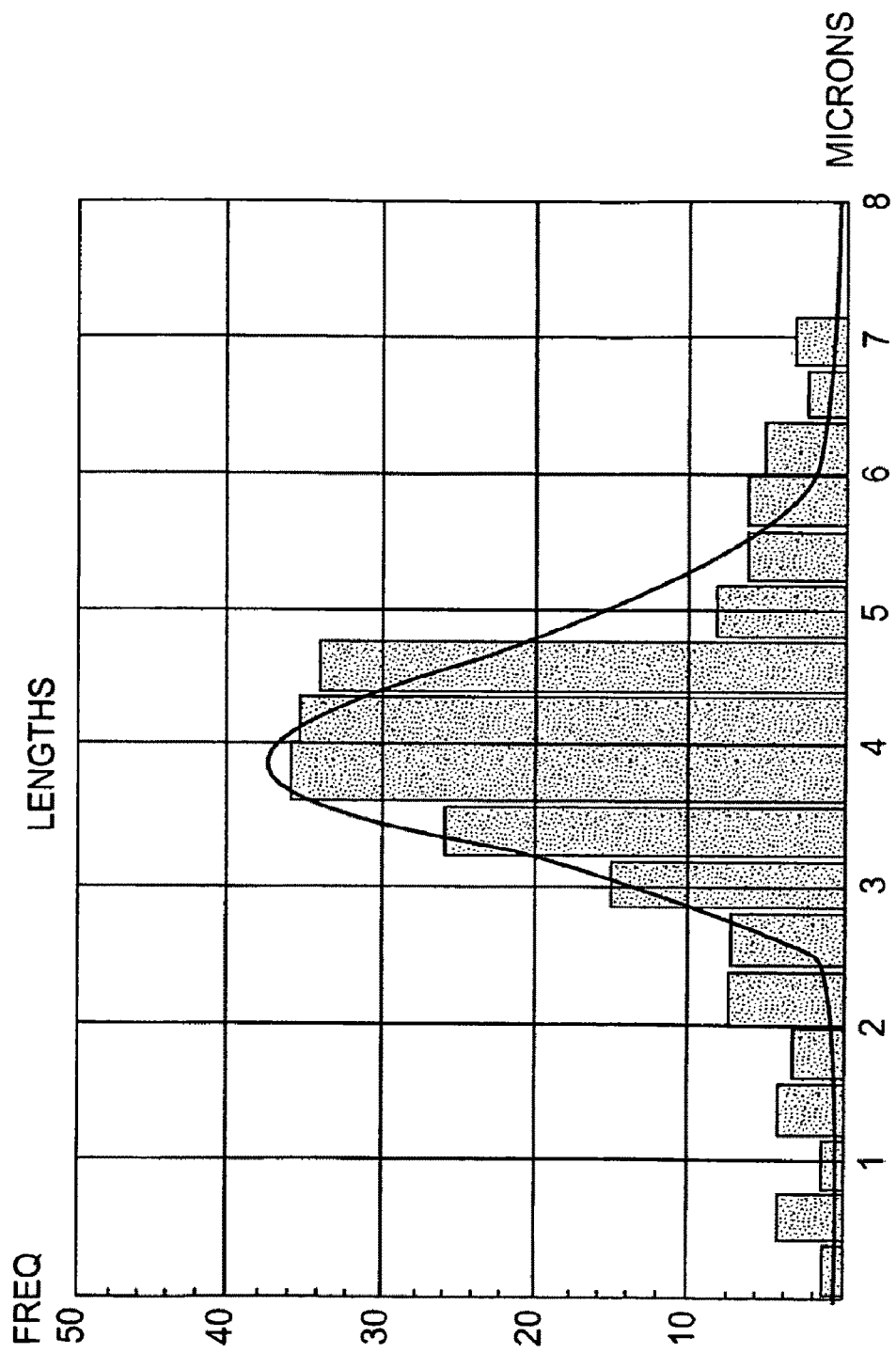

PROCESS AND APPARATUS FOR MEASUREMENTS OF MUELLER MATRIX PARAMETERS OF POLARIZED LIGHT SCATTERING

CROSS-REFERENCE TO RELATED APPLICATIONS

This application is a continuation of International Patent Application No. PCT/US06/38463 filed on 3 Oct. 2006 and entitled "Process and Apparatus for Making Measurements of Mueller Matrix Parameters of Polarized Light Scattered." International Patent Application No. PCT/US06/38463 claims priority to U.S. Provisional Patent Application No. 60/722,405 entitled "Process and Apparatus for Making Measurements of Mueller Matrix Parameters of Polarized Light Scattered" filed Oct. 3, 2005. PCT Application No. PCT/US06/38463 and U.S. Provisional Patent Application No. 60/722,405 are hereby incorporated by reference in their entirety.

RIGHTS OF THE GOVERNMENT

This invention was made, in part, with support from Air Force Contract F33615-00-2-6059, and the United States Government may have certain rights to this invention.

BACKGROUND

1. Field of the Invention

This invention is directed to a system and process for measuring Mueller matrix elements, in particular, with utilization in biological warfare. The present invention is also directed for use in quality control for manufacturing of micron-sized particles of various shapes to determine the extent of deviation from design parameters for members of a batch of particles, for use in rapid classification of the types of cells contained in a particular tumor or other biological samples, and for use in quality control of various powders manufactured for pharmaceuticals and other applications.

2. Description of the Background

The Mueller matrix is the transfer matrix in the Stokes algebra that describes the polarization of natural light. It can be used for comparison with theoretical calculations as well as the determination of material parameters. The Mueller matrix is an important parameter in the study of polarization configuration associated with light-scattering and radiative transfer processes.

Mueller matrix elements are used for such systems as small particle, or a collection of particles, or any other scattering system to give all the characteristics of that system for scattering polarized light (Bohren and Huffman, 1983; van der Hulst, 1957). It has been shown both experimentally and theoretically, that measuring some of these parameters as a function of scattering angle, gives information on the size, shape and optical constants of collections of biological particles (e.g., Bohren, 1983; Van der Merwe et al. 1992, 1995).

One application of such measurement produced a rapid measure of the toxicity of certain compounds of bacteria (Bronk et al. 2001) and rapid measurement of changes of bacterial cell size in vivo (Van der Merwe et al., 1997). As comparable optics become available for the IR ranges (e.g. about 10 micrometers) suitable for large cells, as are now available in the visible and near IR, similar measurements will have important medical applications for rapid examination of disaggregated mammalian cells (e.g., from biopsies) after various treatments.

In this time of war and terrorism, preparation for new methods of attack on armed forces is important. Attack by deliberate exposure to a biological pathogen is likely to be in the form of an airborne microorganism. Thus, there is a need for an efficient and inexpensive method and apparatus for obtaining classification information of an aerosol.

SUMMARY

The present invention overcomes the problems and disadvantages associated with current strategies and designs and provides new tools and methods for quickly measuring Mueller matrix elements of particles for use in classifying airborne particles.

One embodiment of the invention is directed to a system for measuring Mueller matrix parameters of polarized scattered light comprising a light scattering apparatus; optical elements; a continuum light source; and a multiple order retarder. Preferably, the system is portable, the continuum light source is a tungsten-halogen lamp and the continuum light source is a mode-locked laser with nonlinear super continuum generating fiber.

The system comprises a light scattering apparatus comprising an input light, at least one polarizing element, a scattering object, at least one output light polarizing element, and a detector. The detector is preferably a charged coupled camera.

In another embodiment, the present invention is directed to a method measuring Mueller matrix parameters of scattered light comprising the system as described herein, setting a linear polarizer so that light is vertically polarized; passing the light through a multiple order retarder wherein a fast axis of said multiple order retarder is set at a particular degree to the vertical; scattering light off a scatterer; passing light through an analyzer set at said particular degree wherein said analyzer is positioned in front of a detector; recording intensity at said detector; and measuring at least one parameter as a function of scattering angle, wherein preferably, the particular degree is 45 degrees. Preferably, the apparatus is calibrated only once during set up.

Other embodiments and advantages of the invention are set forth in part in the description, which follows, and in part, may be obvious from this description, or may be learned from the practice of the invention.

DESCRIPTION OF THE INVENTION

Figure 1:
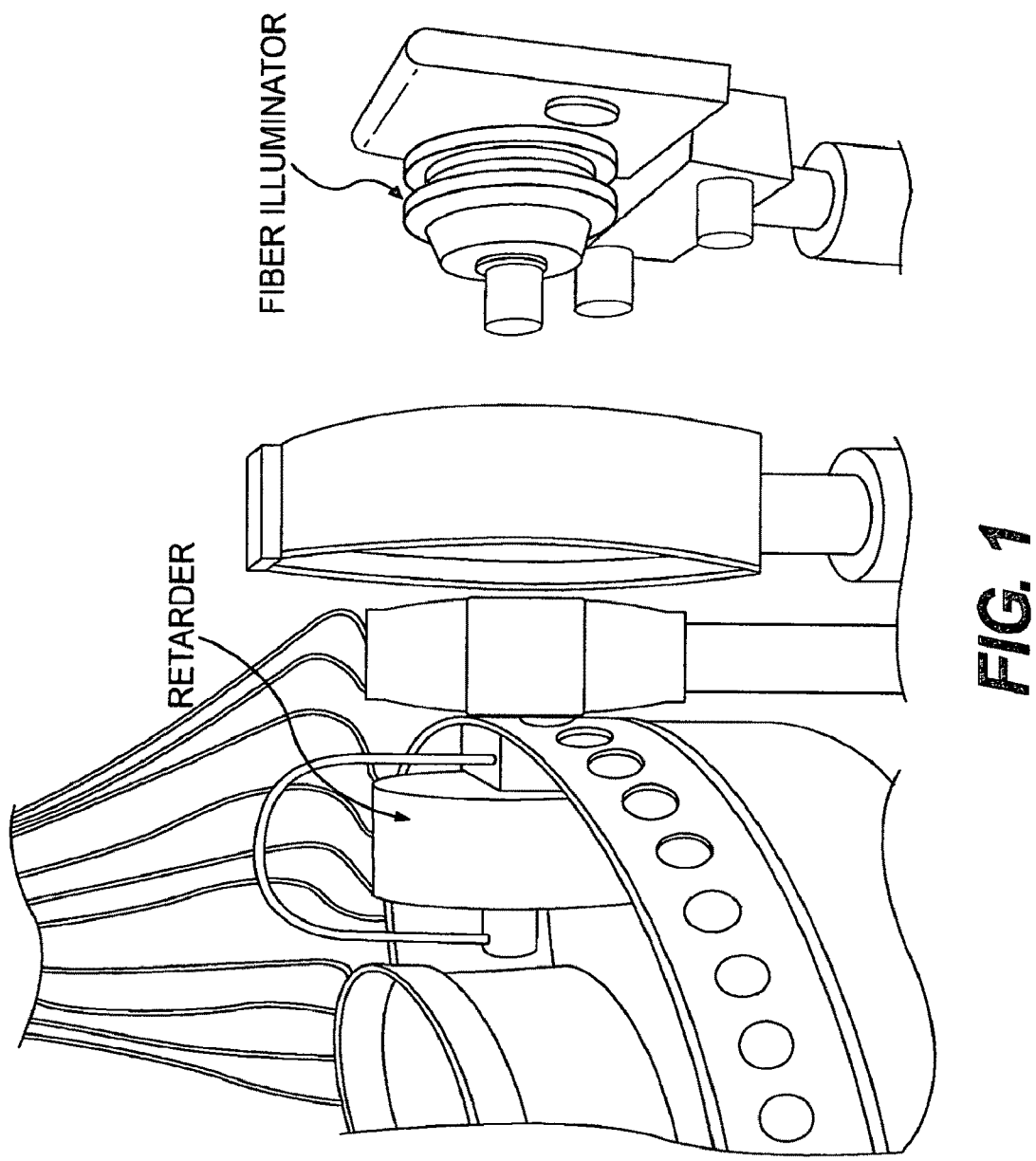
FIG. 1 Input Light Conditioner

There are several drawbacks to the presently available method of measuring Mueller matrix elements. Many of these commercially available methods are described in texts (e.g., Bohren and Huffman, 1983) and require complex and expensive apparatus involving a lock-in amplifier. These apparatus involve sensitive instrument known as a photoelastic modulator or other type of variable optics. They can rapidly vary the retardance of one polarization of the light incoming to the scattering system or object.

These instruments, particularly the variable retarder, are delicate, and not readily adaptable to a portable instrument in which portability means could be easily carried from place to place. Nor can the available instrumentation for these measurements be packaged in a way to be easily set up by laboratory personnel without advanced physics or optics training.

A further drawback of the available method is that the instrumentation must be reset after a measurement when the Mueller matrix elements for more than one wavelength are to be measured. This and all problems associated with the conventional apparatus and method noted herein are overcome with the method and apparatus of the invention.

As embodied and broadly described herein, the present invention is directed to process and apparatus for measuring Mueller matrix parameters of polarized light scattering. Preferably, the present invention is used for classifying information regarding aerosol particles of biological pathogens used in bioterrorism.

The method of the invention can be packaged as a complete single instrument by a commercial instrument maker in a manner similar to the way fluorometers or spectrometers are sold so that calibrating instrumentation is included in the package in a way in which assembly is completed by simply following calibration instructions.

One important aspect of the new invention deals with its application to single particles. For almost all the Mueller matrix elements, at least two and preferably more than two measurements at different polarizations must be made on an object to determine the value of the element. A flow-thru system like a flow cytometer is desirable for measuring single particles so that many particles can be compared. For such a system at a reasonable rate of flow (e.g., about 2 m/s), the time the particle is in the measuring volume is too short to allow multiple measurements of the sort needed. The method of the invention measures the intended Mueller matrix elements in a single step without the need of any change in the optics, so it scales down to any short time interval depending only on the intensity of the input light or the sensitivity of the detector.

With the method and apparatus of the invention, the matrix elements can be measured for many different wavelengths from a broadband source simultaneously (e.g., from 400 to 800 nm). Measurements made over a range of wavelengths provide information comparable to measurement over a range of angles and may provide additional information as well. This is a surprising and considerably improvement over conventional procedures.

Previously published methods utilized an electronically vibrating optical element, such as a photoelastic modulator, to rapidly switch polarizations from left to right circularly polarized and back. Using this instrument, and a small number of fixed optical elements such as polarizers, any of the sixteen Mueller matrix elements could be measured. This invention provides a new and surprising method of accomplishing the same result, but requiring an intrinsically simpler element with no moving parts and without the need of changing any optical parameters. Advantages of the present invention include simplifying optical apparatus to use in bioterrorism when speed and efficiency are concerns.

The present invention provides a new and surprising method and apparatus for measuring a single particle scattering where the particle flies through the measuring device in a relatively short time. The size, shape and optical characteristics of the aerosol particle obtained by light scattering measurements give classification information that can be automatically correlated with spectral information obtained with multivariate optical elements (MOE).

The method of the invention utilizes variation in retardation over wavelength as opposed to variation in retardation with time as is achievable with the photoelastic modulator or a variable modulator. Retarders are considered better if they are broadband so that retardance changes slowly with wavelength. In the present invention, a retarder was used having several retardance cycles over the spectral range detected. Orienting its fast axis at 45 degrees to a polarizer, a nearly periodically changing polarization with as many periods desired was obtained. To utilize the method, a multiple order retarder is required in addition to the usual fixed optical elements and a continuum light source. For the continuum light source, a standard tungsten-halogen lamp may be used, or more preferably, the recently developed method of using a mode-locked laser with the nonlinear super continuum generating fiber.

Optical retarders are commercially available from various optical supply houses (e.g. Coherent, Ealing Electro-optics, Elliott Scientific Ltd., Newport Corp., OptoSigma). The retardation angle, delta, can vary from zero radians to $2\pi$ radians multiplied by many factors. The effect can be visualized as two coherent in-phase light waves that are first separated, then recombined. The phase of one light wave is retarded by the angle delta. For example, if the retardation delta is $\pi/2$ (zero order, quarter wave retarder), the recombined beams would be circularly polarized. For such an application, it is preferable to have the retardation only slowly varying with the wavelength so that the apparatus is not sensitive to small wave-length changes.

Multiple order retarders are available which are constructed so that the effective retardation angle is some phase angle less than $2\pi$ plus several full wave retardations. In this case the excess phase angle (mod $2\pi$) retardation is a rapidly varying function of wavelength. These retarders are also available from standard sources. Thus, with a continuum light source, the retardation can often vary through several times $2\pi$ if the wavelength varies over the bandwidth available.

For a useful size of particle scattering to be examined by Mueller matrix technology, the matrix elements for a fixed angle generally vary only slowly with wavelength. For instance, the combination of left and right circular polarization for a fixed wavelength by comparing the result for two wavelengths which are only separated by a small enough difference to have a negligible effect on the matrix element of interest which can be compensated for by mathematical interpolation can be approximated. Thus, variation over time has been replaced by variation of retardance over wavelength.

In one embodiment, a retarder is placed between crossed polarizers and the spectrum of white light before and after the analyzer is measured to determine the change of the retardance with the wavelength. Two matrix elements S34 and S12 are utilized. A "white" light is passed through the first element, a linear polarizer, set so that light is vertically polarized. Next the light passes through the multiple order retarder where the fast axis of the multiple order retarder for the wavelength band is set at 45 degrees to the vertical. Light scatters off the scatterer and then passes through a 45 degree analyzer placed in front of the detector. The intensity recorded at the detector becomes proportional to $$S11+S31-(S12+S32)*Cos(x)-(S14+S34)*Sin(x). \quad (1)$$

where x is the retardance. For spherical homogenous particles, or a randomly oriented collection of particles which is spherically symmetric, the expression simplifies to $$S11-S12*Cos(x)-S34*Sin(x) \quad (2)$$

as S31, S32, and S14 become very small or zero. The method with a suspension of spherically symmetric particles is verified with the formulas.

From formula (2) the wavelength dependence of the retardance, then upon fitting the above formula to the wavelength dependence of the scattered light at a particular angle yields the wavelength dependence of the S11, S12, S34 parameters at that angle. Other matrix element combinations can be measured with appropriate combinations of the polarizers and retarders in the input and output light paths.

Every light scattering apparatus comprises the following main components: input light, polarizing element, scattering object, output (scattered) light polarizing elements, and detector.

In another embodiment, a vertical polarizer is followed by a multiple order retarder to set the state of polarization of the input light. A bundle of optical fibers is used to collect the scattered light at several scattering angles simultaneously. Before the input end of the fibers polarizers are set at 45 degree to the horizontal (scattering) plane, one end of each of the fibers is set to measure on end of several evenly spaced angles around the spectrograph which maps the angles in one dimension and the output wavelengths in the other. The output of the imaging spectrograph is detected using a sensitive charge-coupled device (CCD) camera. The input light conditioner is shown in FIG. 1.

Figure 2:
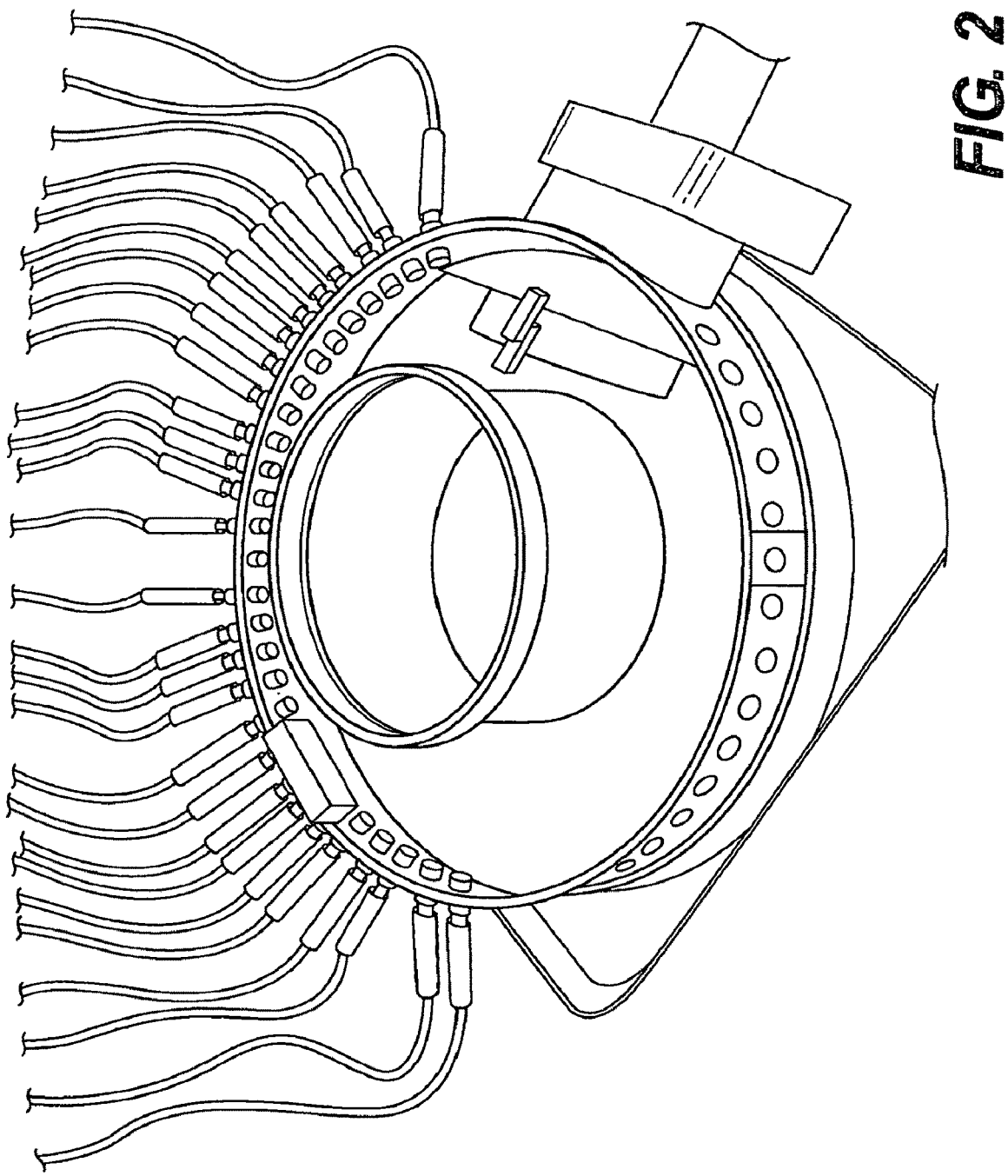
FIG. 2 Light Collector Unit
Figure 3:
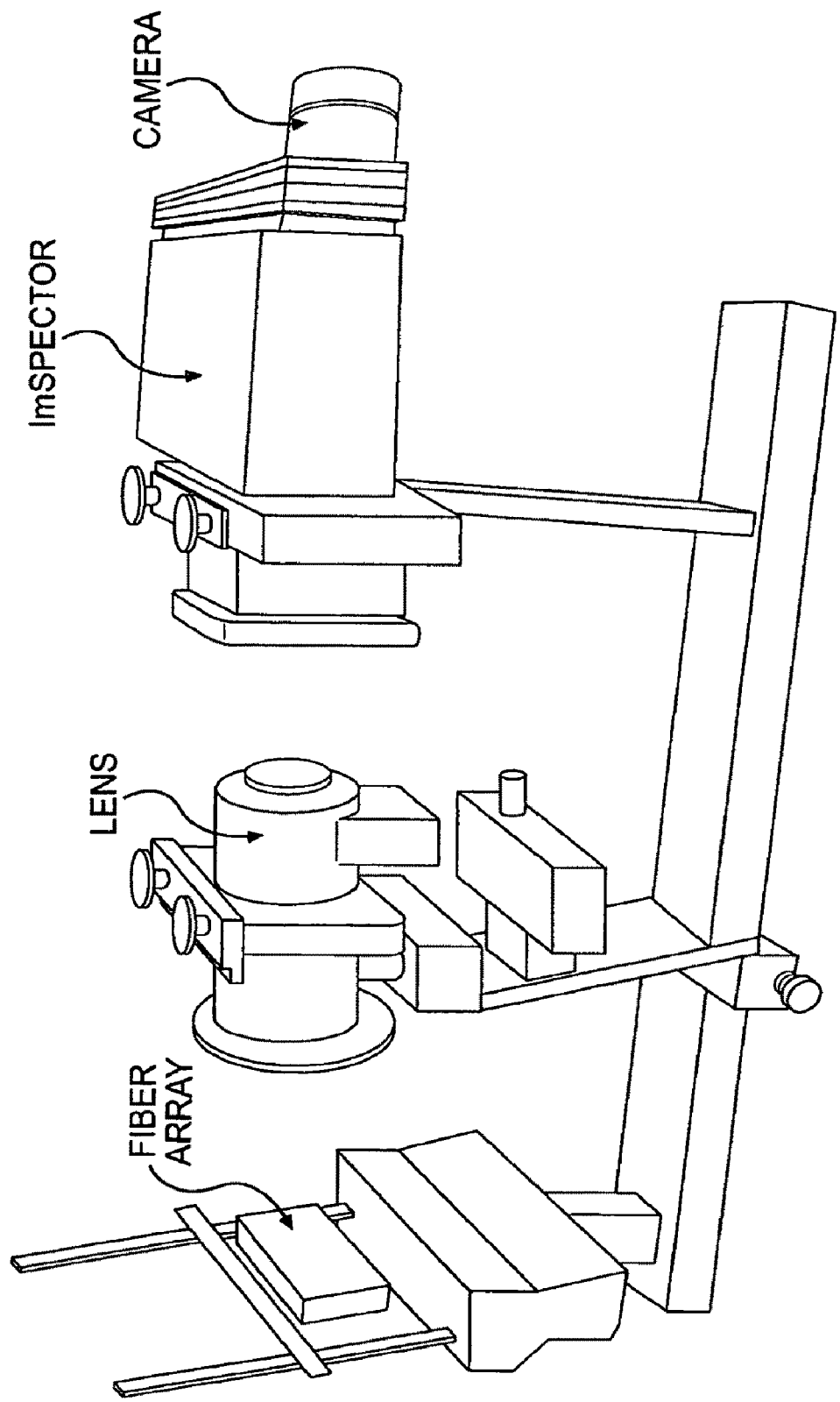
FIG. 3 Detector Unit
Figure 4:
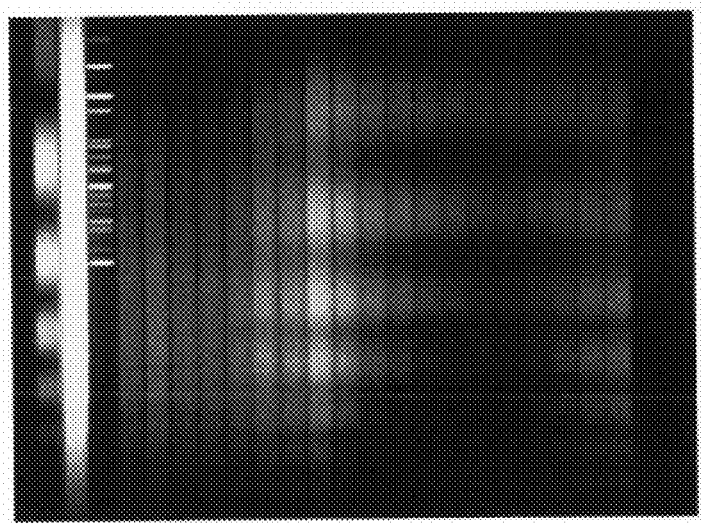
FIG. 4 Typical Camera Frame

FIG. 2 shows the array of optical fibers arranged around the scattering object while FIG. 3 indicates how the lined-up fibers are coupled to the imaging spectrograph which is furnished with a CCD camera. FIG. 4 shows a typical camera frame with vertical stripes giving the wavelength dependence of the scattered light at a particular scattering angle.

A black border is shown at the left in FIG. 4. Counting to the right from the border, the first oscillating stripe gives the wavelength dependence of the zero angle beam after passing through a horizontal polarizer. The nodes or centers of zero intensity mark the points where the retardance is an integral multiple of $2\pi$ so that retardance can be calibrated at every wavelength. This stripe can be taken with the sample in place because a properly prepared sample should be dilute enough to avoid multiple scattering so it will not alter the polarization noticeably for zero angle. White indicates high intensity. The wavelength dependence is vertical in each stripe with red on the top and blue on the bottom. The next "white" appearing stripe to the right is the broad spectrum of the white lamp used, which numerically indicates degrees of shading. This can be taken at very low scattering angle or, alternatively, removing the sample and using the same channel as for the retardance calibration. The next vertical stripe gives the bright lines of a mercury and a neon lamp used for vertical wavelength calibration. These three channels need only be measured once, when setting up the instrument.

From this point to the right, FIG. 4 shows a typical camera frame when the setup is as described below with scattering from 503 nm spherical polystyrene beads suspended in water in the dish shown in FIG. 2. Counting stripes from here, each stripe is a spectrum of the scattered light at a particular scattering angle. The angles range from 20 to 140 degrees spaced evenly with 18 intervals. Other than for the calibration at zero degrees, a polarizer at 45 degrees is placed in front of each fiber at the exit opening from the scattering dish. In one embodiment, this was performed with a polarizing sheet.

In additional embodiments, the following procedures are preferably performed.

a. The digital camera coupled to the imaging spectrograph must be calibrated as a unit. This will assign a wavelength to the camera frame pixels in the vertical stripes seen in FIG. 4.

b. To be able to use Formula (1), the retardance as a function of the wavelength can be determined. A vertically polarized beam is allowed to go through a retarder with its fast axis at a 45 degree angle to the vertical. Then, at 0, $\pi/2$, $\pi$, $3\pi/2$, $2\pi$, . . . , etc. retardances, polarized light vertically, left circularly, horizontally, right circularly, vertically, etc. results with elliptically polarized light at intermediate retardances. When a horizontal polarizer (analyzer) is placed just after the retarder with no scatterer, these changes are illustrated by a computed graph as in FIG. 5.

Figure 5:
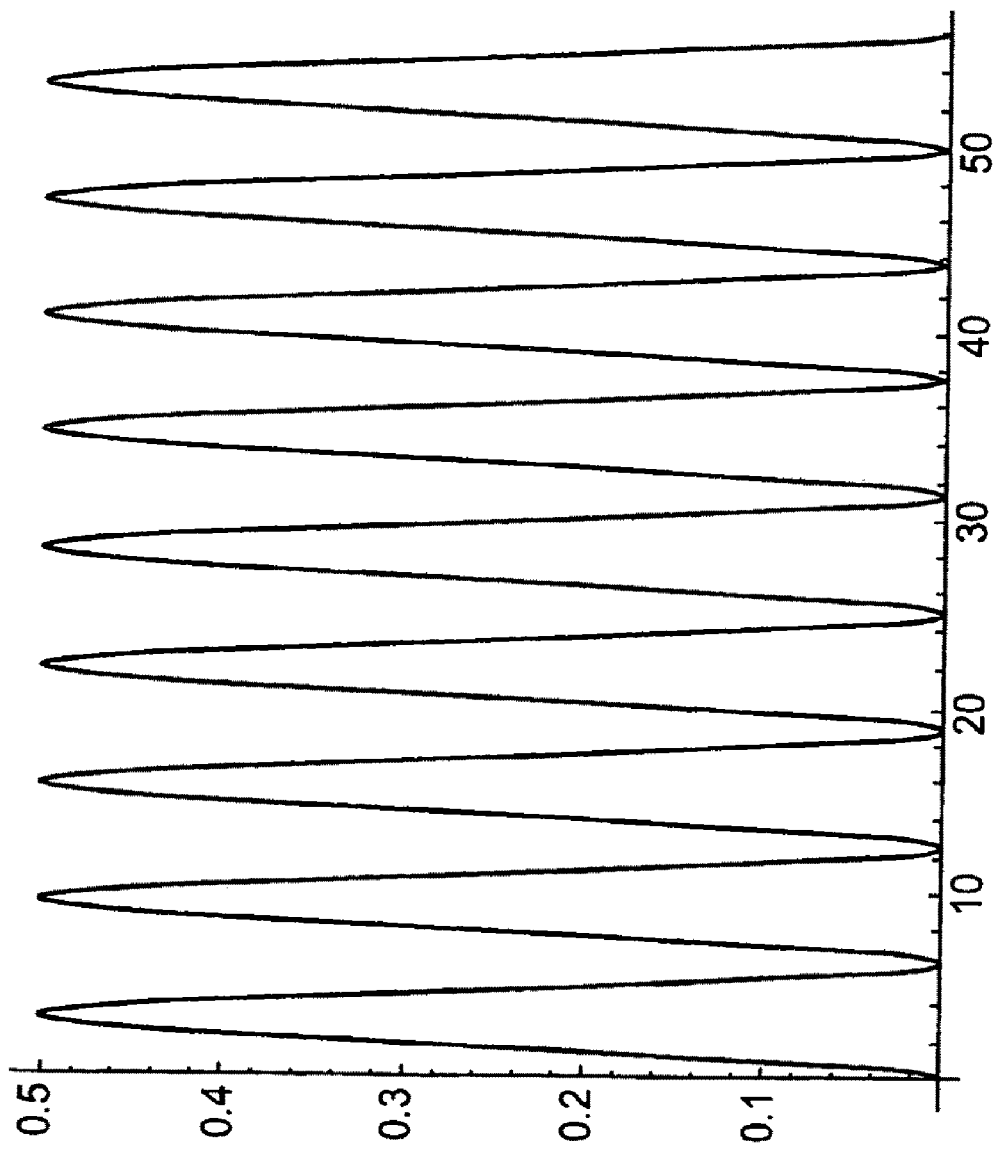
FIG. 5 Computed Graph for Idealized Dependence of Light Intensity
Figure 6A:
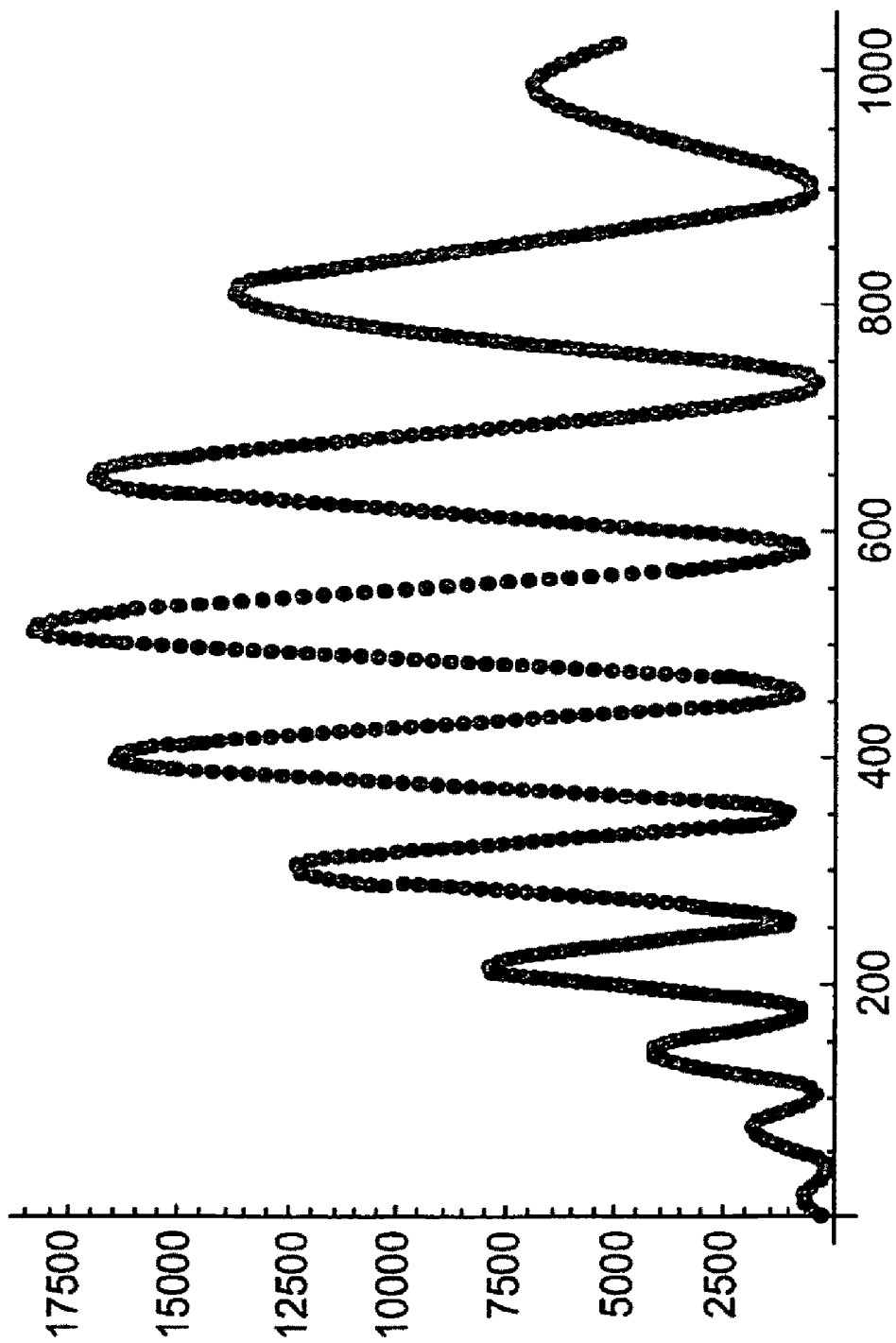
FIG. 6a Experimental Measurement to Determine $x(\lambda)$

Putting the properly oriented retarder between crossed polarizers and measuring the spectrum of white light before and after the analyzer, the change of the retardance with the wavelength can be determined. A typical measurement is shown in FIG. 6a. The idealized result shown in FIG. 5 is used to determine the dependence of the retardance of retarder on the wavelength. If the difference between the ordinary and extraordinary index of the retarder did not depend on the wavelength then the retardance could be simply calculated from the d thickness, the $\Delta n$ index difference and the $\lambda$ wavelength:

$$x(\lambda)=2*\pi*d*\Delta n/\lambda \quad (3)$$

In this embodiment, however, slow wavelength dependence must be accounted for the index difference, $\Delta n$. The precise empirical retardance shown in FIG. 6c is obtained when data in FIG. 6a is normalized with the lamp spectrum in FIG. 6b and imperfections of the analyzer are accounted for.

Figure 6B:
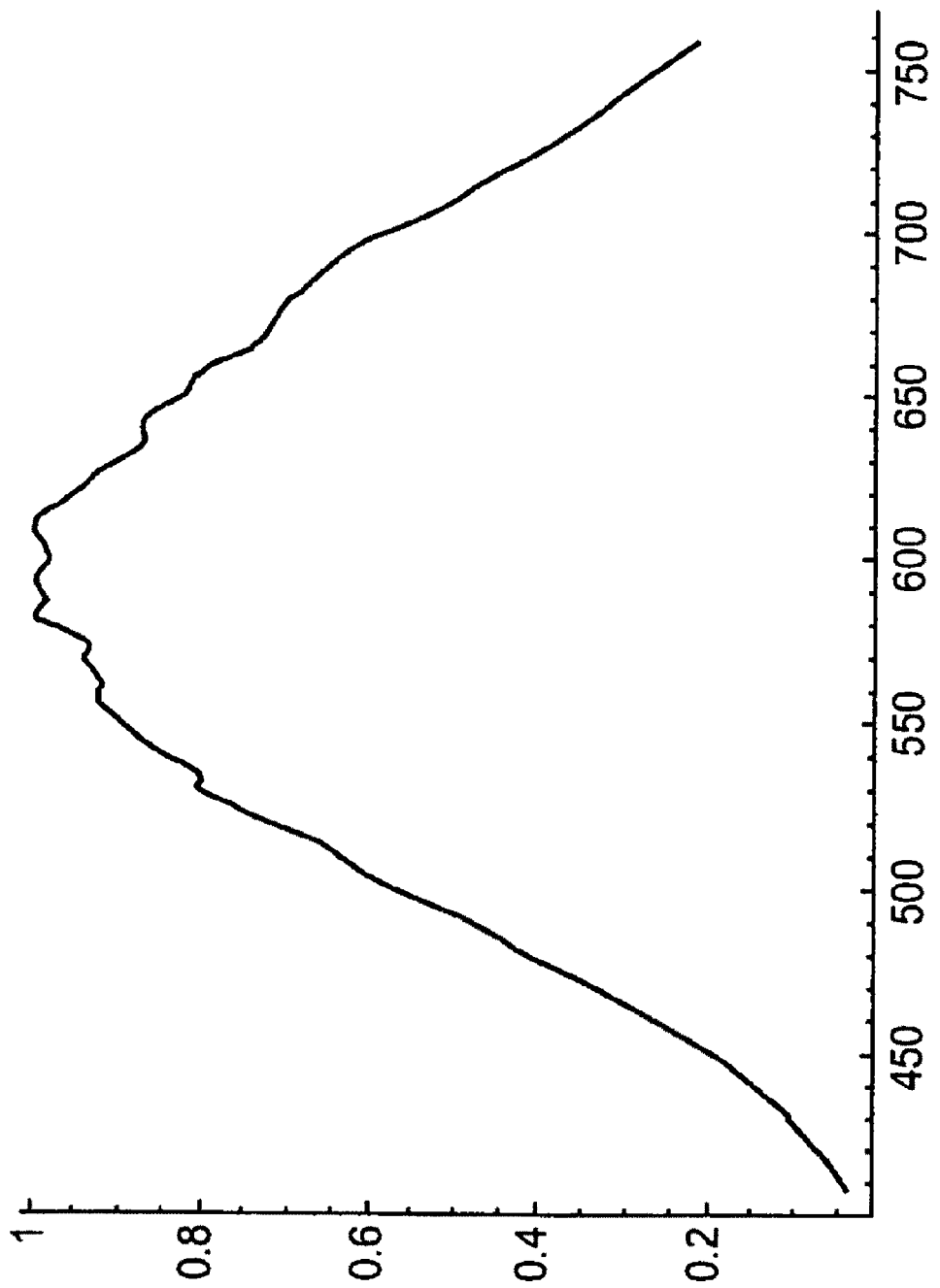
FIG. 6b Graph of Spectrum of Input Light after Polarizer and Retarder
Figure 6C:
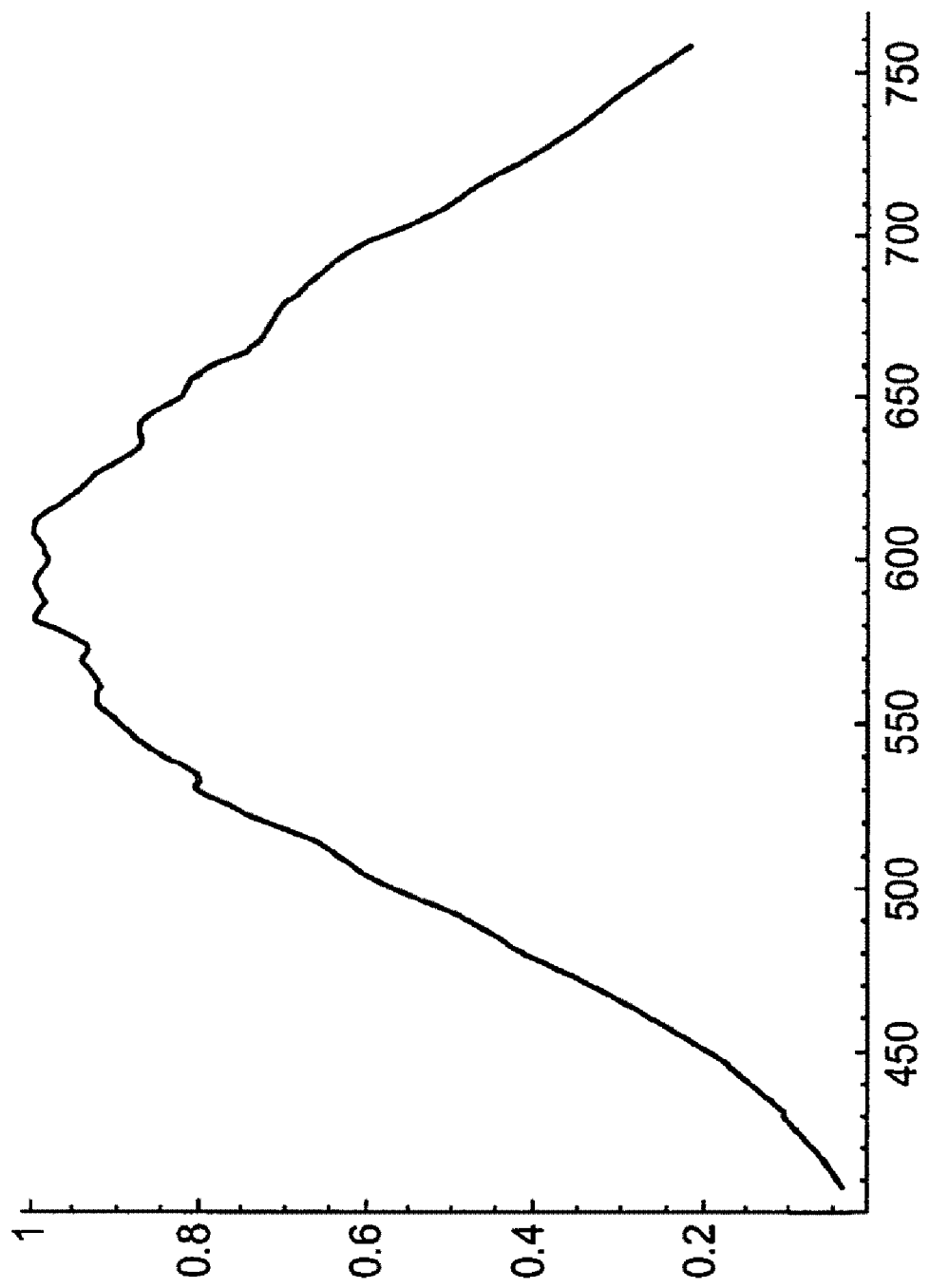
FIG. 6c Final Calibration Data After Normalization

The graph of FIG. 6a is related to the graph of FIG. 4, but the horizontal axis in FIG. 6a is proportional to wavelength, and the amplitude is attenuated by the wavelength profile of the lamp (FIG. 6b). The vertical axis measures the intensity of the exposure corresponding to the first stripe after the black border on the left of FIG. 4.

As $\Delta n$ is a slowly varying function of the wavelength, the equation is:

$$x=(C/\lambda)(1/\lambda+C_{10}+C_{11}\lambda+C_{12}\lambda^2+C_{13}\lambda^3) \quad (4)$$

where $C=2*\pi*d$, and the $C_{1j}$ are variable parameters to be fit by the calibration data.

In FIG. 6b, the spectrum of the "white" lamp is used. Data is normalized in FIG. 6a by dividing by this spectrum over the wavelength range to be used and readjusting the maximum intensity to one.

FIG. 6c depicts the final normalized calibration curve after normalization with the input light spectrum and minor adjustment for other elements. Transforming the x axis of the curve of FIG. 6a with the polynomial fit for the retardance obtained using eq. (4) results in a precise fit to this experimental curve which exactly overlaps it on the scale of FIG. 6c.

Figure 7:
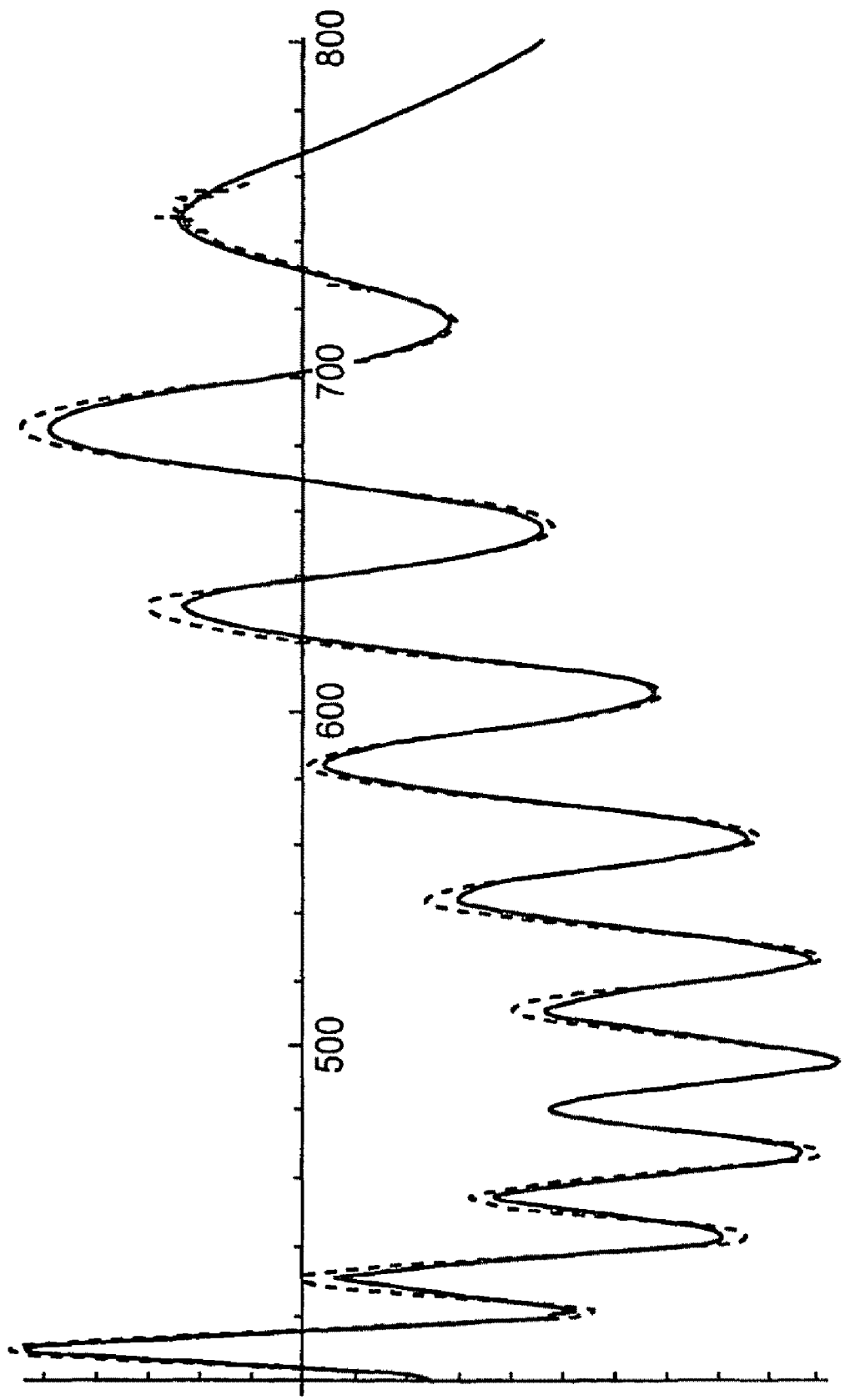
FIG. 7 Graph of Typical Fit of Expression (2) to Experimental Data

FIG. 7 depicts an experimental graph corresponding to the intensity measured at the camera after scattering from 503 nm beads as a function of wavelength for a particular angle. Expression (2) applies to the result because the beads are spherical. To determine the three matrix elements of (2) the data using multinomial expression of S11, S12 and S34 are fit to the following formula:

$$S_{ij} = A_{ij-1}/\_ + A_{ij-0} + A_{ij1}\_ + A_{ij2}\_^2 \quad (5)$$

There are a total 12 unknown coefficients, for the three matrix elements which were determined by the best fit to 1024 data points for each individual angular strip. The fit for a particular angle is shown in FIG. 7. The typical fit (red) of the empirically determined expression (2) to the experimental data (black) is depicted. The horizontal axis represents the wavelength in nm. The graph (black) is a fit using expression (5) with the 12 empirical constants for this angle. These curves come from a 503 nm bead scattering measurement in the 53.33 degree channel.

Figure 8A:
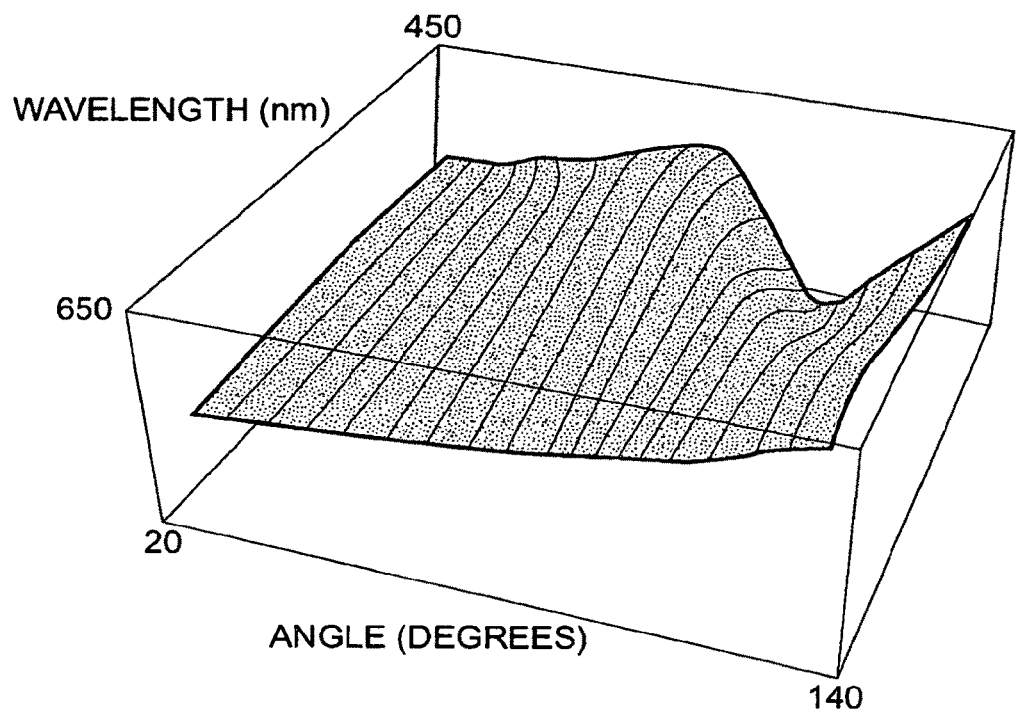
FIG. 8a S34/S11 Matrix Element Surface for 300 nm Spherical Polystyrene Beads
Figure 8B:
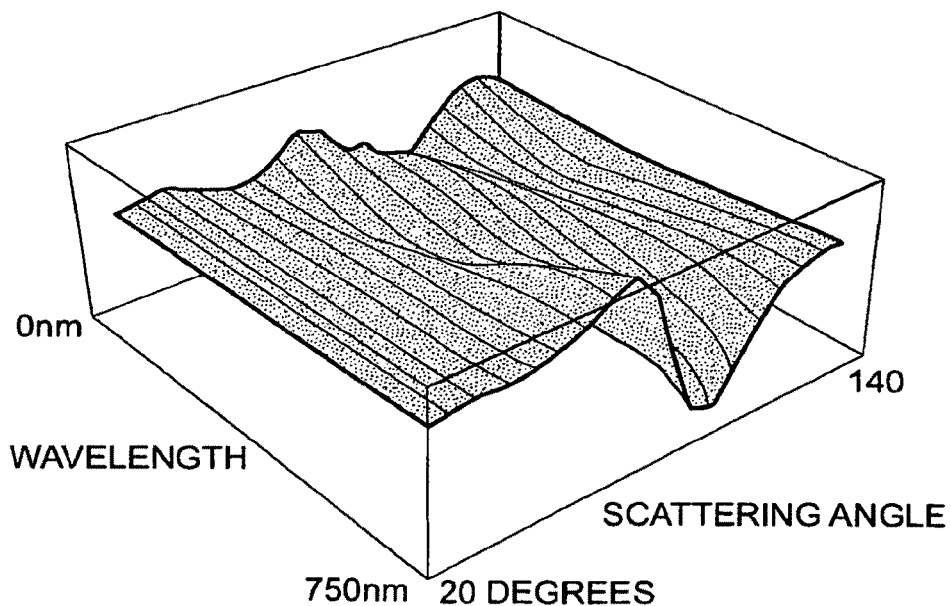
FIG. 8b S34/S11 Matrix Element Surface for 503 nm Spherical Polystyrene Beads

Ratios for S34/S11 were assembled from the various angular curves into a smooth two dimensional surface. The resulting surfaces are depicted in FIGS. 8a and 8b. FIG. 8a shows the S34/S11 for 300 nm beads while FIG. 8b is the same surface for 503 nm beads.

Figure 9A:
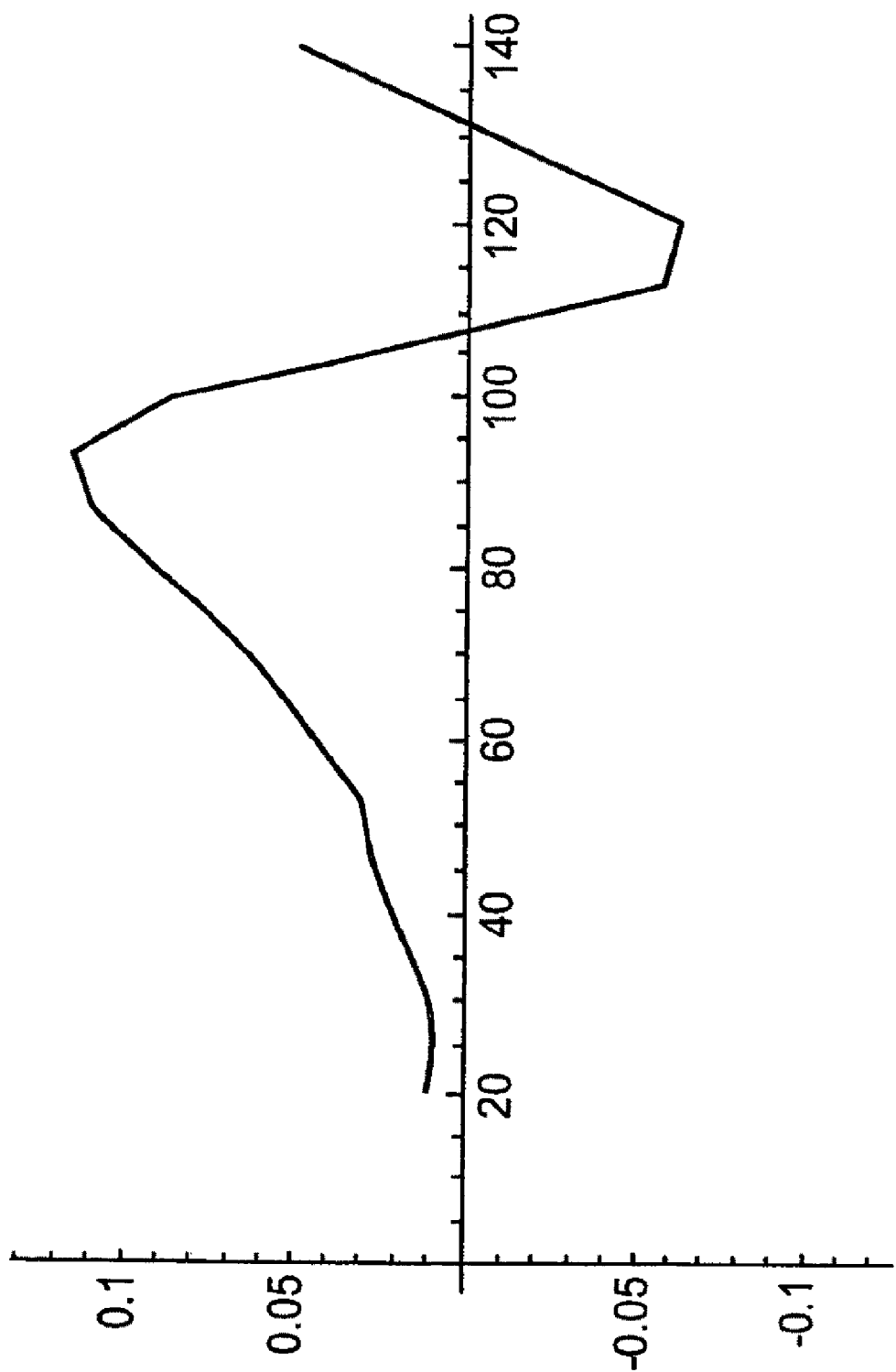
FIG. 9a Scattering Angle Dependence of S34/S11 Matrix Element for 300 nm Spherical Beads at 500 nm Wavelength FIG. 9b Scattering Angle Dependence of S34/S11 Matrix Element for 503 nm Spherical Beads at 500 nm Wavelength FIG. 10 S14/S11 Matrix Element Measurement for 300 nm Spherical Beads at 500 nm Wavelength FIG. 11 Scattered Light Spectra from 5000/s Particle Stream with 20 Seconds Exposure Time FIG. 12 Typical Microscopic Image of the NaCl Particles Collected on a Microscope Slide FIG. 13a Particle Area Distribution in Pixel Units FIG. 13b Distribution of the Diameter of the Bigger Particle Population with Lognormal Distribution Fit FIG. 13c Distribution of the Diameter of the Smaller Particle Population with Lognormal Distribution Fit
Figure 9B:
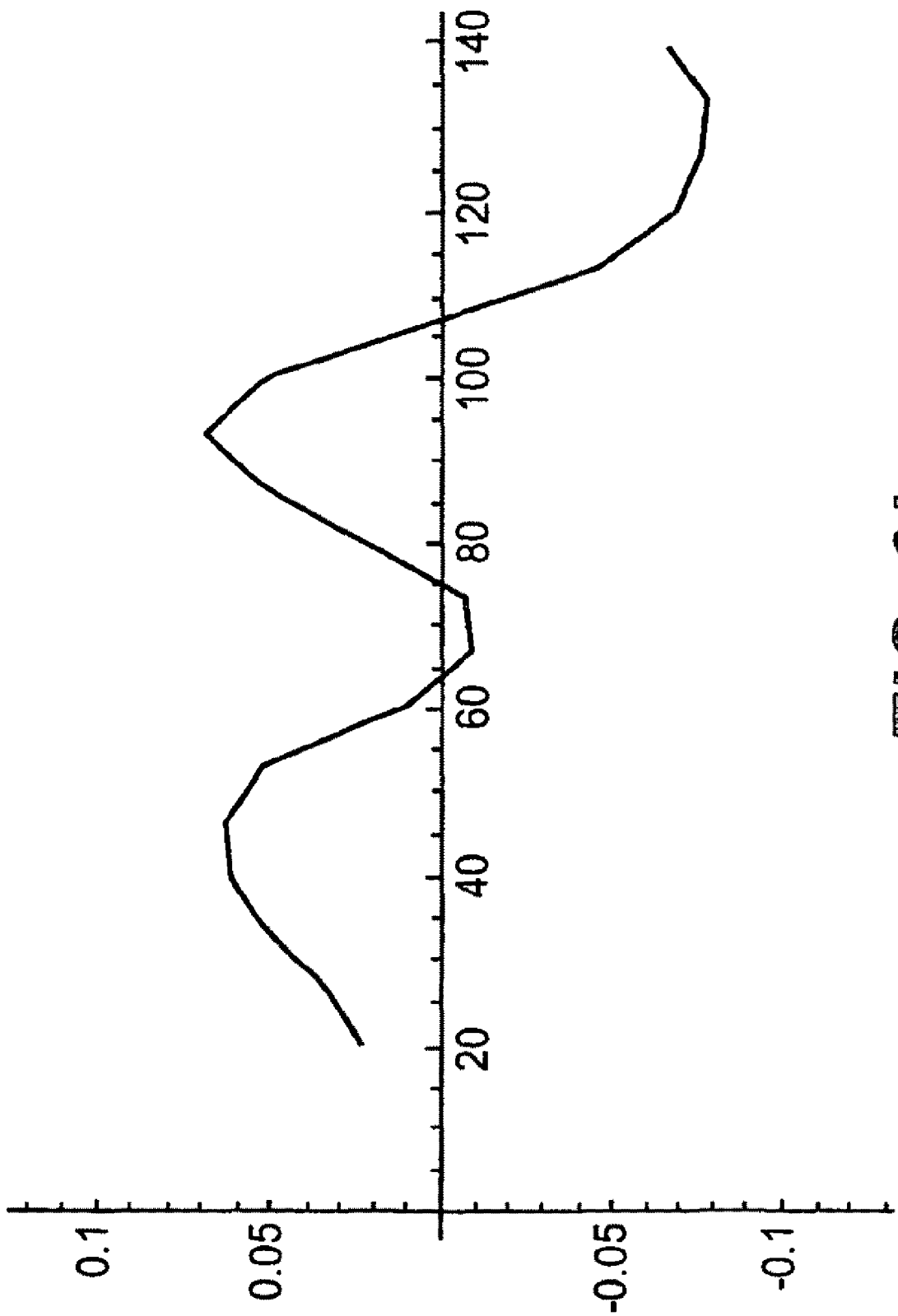

FIGS. 9a and 9b show a projection of FIGS. 8a and 8b on the plane of constant wavelength at 500 nm wavelength for 300 nm and 503 nm beads, respectively.

Figure 10:
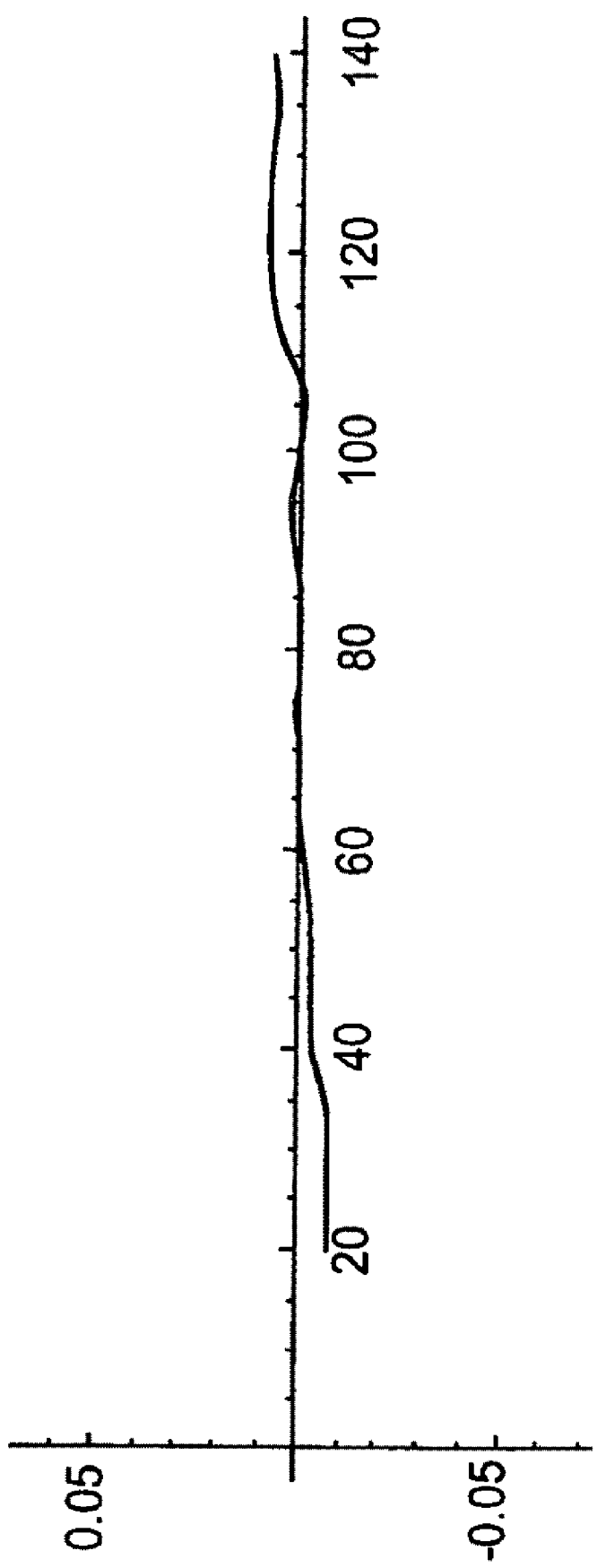

Necessary modifications of the optics were performed to obtain S14 in a similar manner used for S34/S11. A graph for S14/S11 for the 300 nm beads at 500 nm wavelength is shown in FIG. 10. The theoretical value of this ratio for homogeneous sphere is zero. The experimental value is consistent with this value within experimental error.

The following examples illustrate embodiments of the invention, but should not be viewed as limiting the scope of the invention.

EXAMPLES

Measurement of Single Particle Polarized Light Scattering

A 1 g/l NaCl solution was put into the cartridge of the an Edgewood particle generator. The column was carefully heated to evaporate solvent from the generated droplets. The process required balance of several parameters: carrier air flow had to be sufficiently low to increase dwelling of the particles in the light beam but fast enough to have them flowing through the beam and not going upward with the warm carrier flow.

Figure 11:
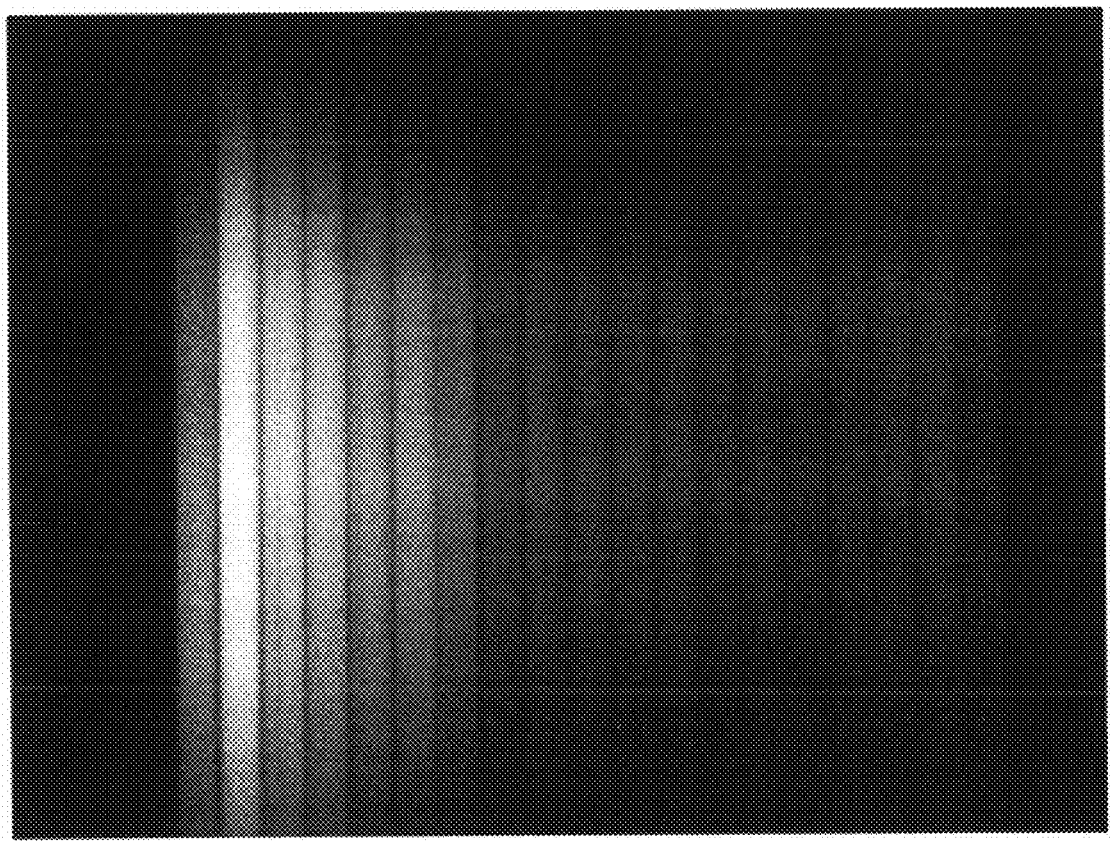
Figure 12:
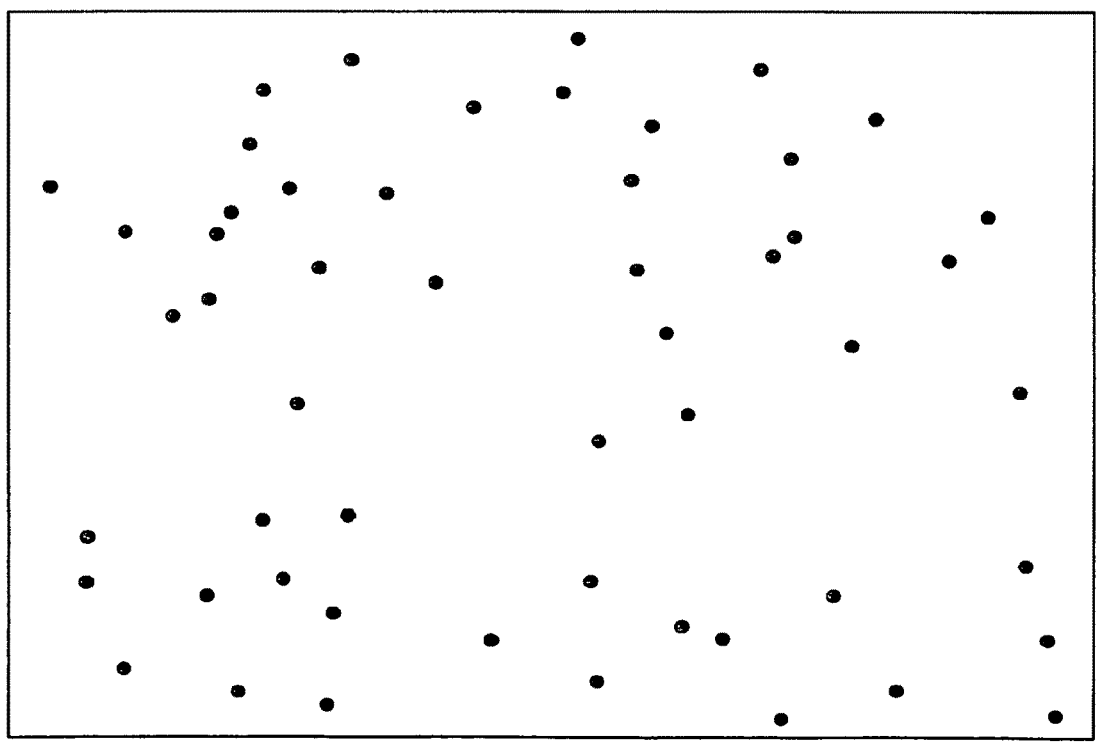
Figure 13A:
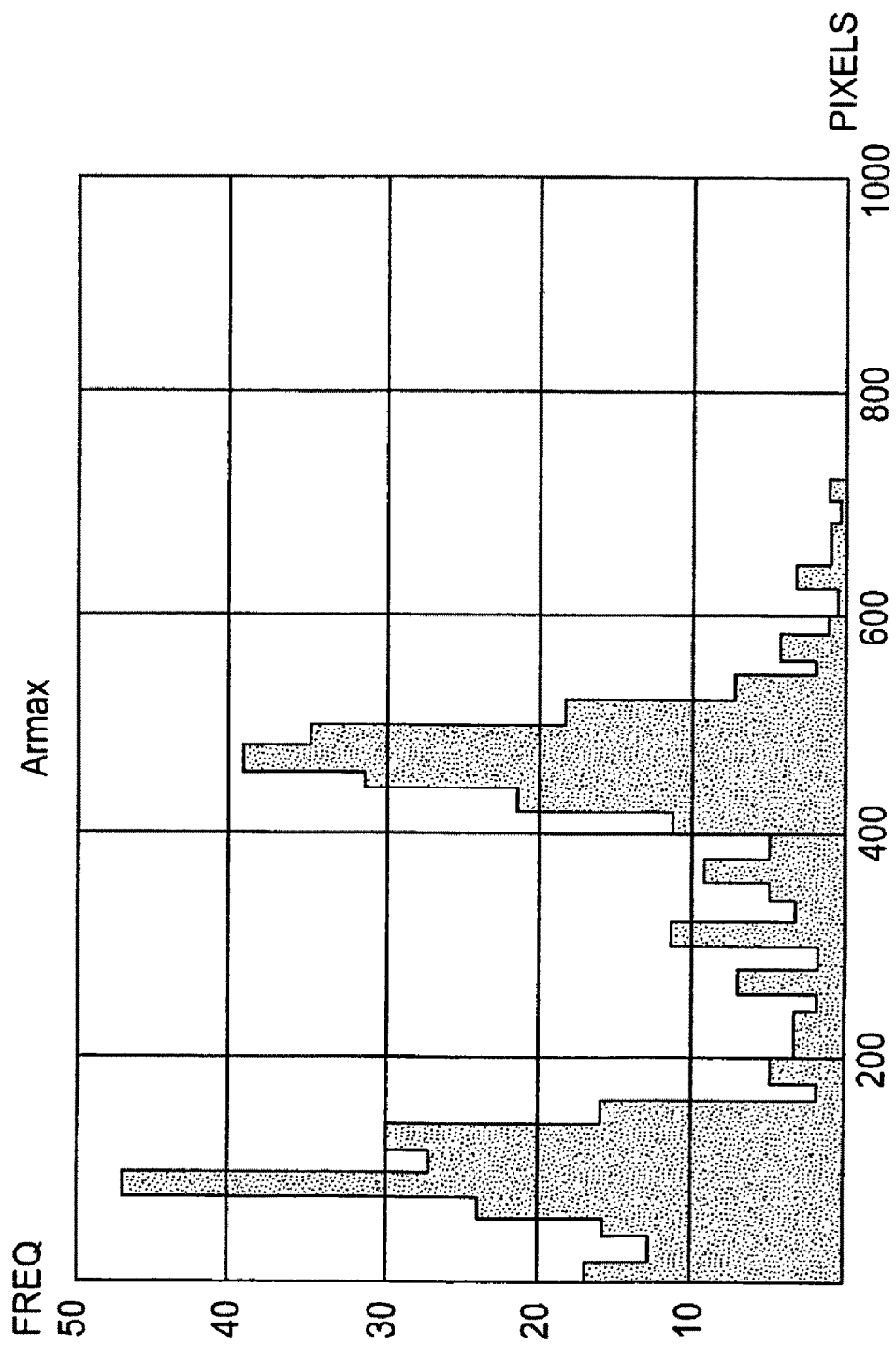
Figure 13B:
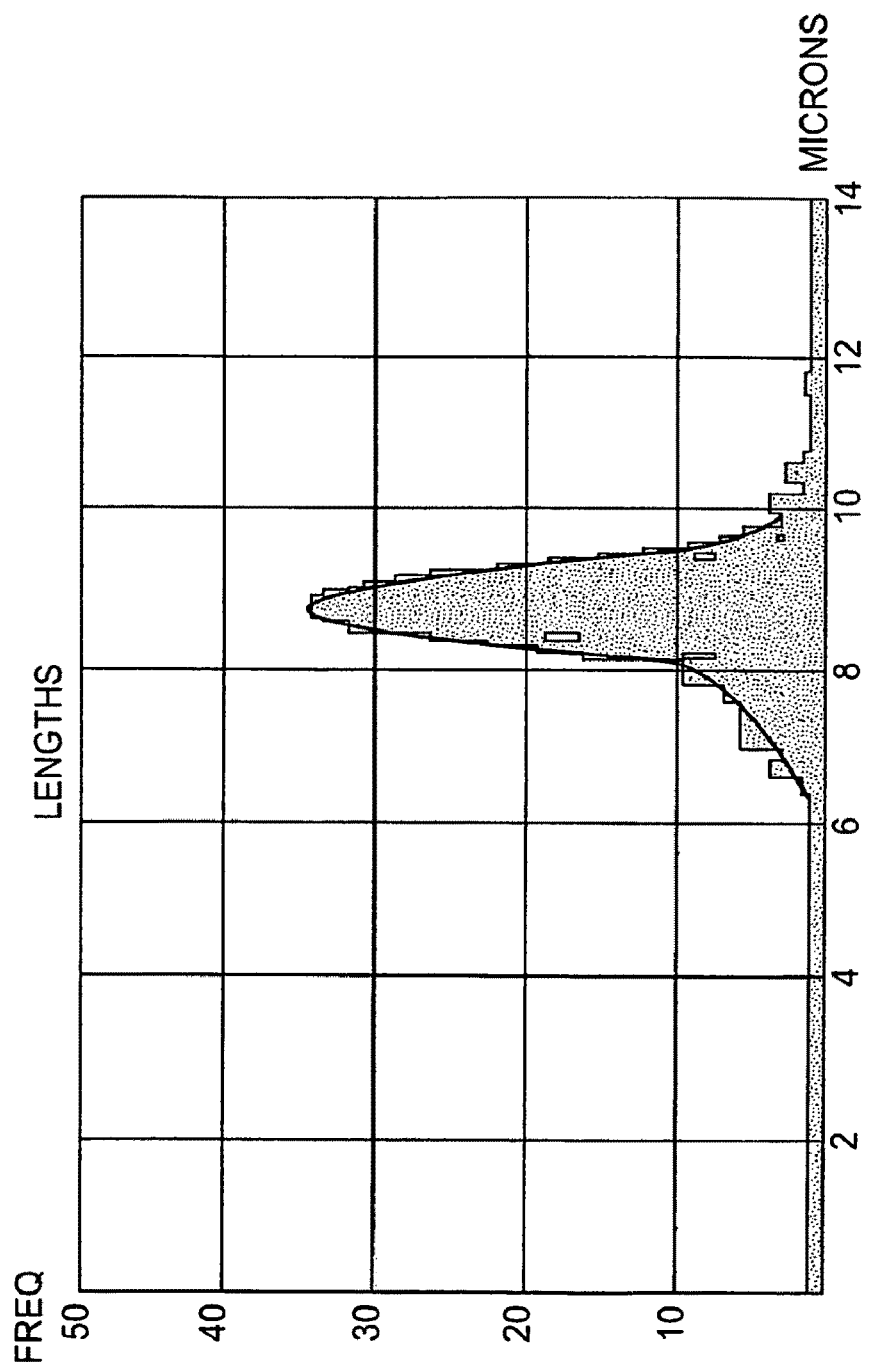

In FIG. 11, the camera frame of the scattering is depicted: the exposure time was 20 seconds, the nominal particle flow was ~5000/s. The evaluation for S12/S11 did not yield any expected S12/S11 pattern. FIG. 12 is a typical microscopic image of the NaCl particles collected on a microscope slide. Therefore, size distribution of particles collected on a microscope slide was measured. Size distribution of the particles was determined by measuring the area of a few thousand spots and calibrating magnification with a stage micrometer. FIGS. 13a-c shows two populations in distribution with ~8 and 4 micrometer diameters. With visible light, in the scattering of big particles, fast oscillations of S12 are expected with the scattering angle which cannot be resolved with the 6.33 degree detector spacing even for the 4 micron particles. Further size reduction did not seem practical taking that the 20 second exposure (with maximal gain) was close to the limit of the SCION camera, the particle generator could not generate more particles, and the intensity of the illuminator also was set to the maximum. To alleviate the problem, infrared was switched up to 1.7 micron wavelength and an intensity scalable super continuum generating illuminator was applied. A low noise cooled camera was use to attempt long exposure, visible measurements on smaller particles. Measurement of polarized scattering from ~3 micrometer particles was attained. Biopsy and tumor use.

As the manufacture of micron-sized particles of various shapes is becoming more and more prevalent, the greater the demand for sorting such sized particles increases. This novel invention is a relatively inexpensive instrument that can measure Mueller matrix elements and used to determine the extent of deviancy from design parameters for members of a batch of particles. Additionally, this invention can be extended into the near and mid infrared range of wavelengths, such as 10 to 12 micrometers. In medical research, it is likely that different human cells will change shape or size in response to various chemical treatments. There are methods which can be used to disaggregate cells from a tumor examined by a biopsy specimen. The Mueller matrix elements obtained from such cells would be able to give a new parameter for rapid classification of the types of cells contained in a particular tumor.

Mammalian Cells.

Many mammalian cells, because they have no cell wall, assume a spherical shape when they are released from binding to other cells or a foreign object and put into a liquid suspension. In that case, the diameter is about 20 microns. In our experience with bacteria, wavelengths from the cells full diameter to slightly less than the full diameter are most convenient for measuring Mueller matrix elements. This means the range of about 10 microns or more. If one obtains an IR laser light source which gives a high intensity in the middle or at the long wavelength end of one of these ranges, and a non-linear fiber which transmits in these IR ranges the present invention is utilized to examiner scattering in two dimensions simultaneously (wavelength and angle) and obtain the Mueller matrix elements for mammalian cells.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

The invention claimed is:

1. A method of measuring Mueller matrix parameters of scattered light comprising:
    applying a light source to a system having a continuum light source that sends light to a light scattering apparatus, optical elements operably connected to the light scattering apparatus, one or more polarizers that polarize light that is received by or passes through the optical elements, and a multiple order retarder set along the continuum light source;
    setting a linear polarizer so that light that passes through the system is vertically polarized;

passing light through said multiple order retarder wherein a fast axis of said multiple order retarder is set at a particular degree to the vertical;

scattering light of a scatterer;

passing light through an analyzer set at said particular degree wherein said analyzer is positioned in front of a detector;

recording intensity at said detector; and measuring at least one parameter as a function of scattering angle.

2. The method of claim 1, wherein the continuum light source is a tungsten-halogen lamp.

3. The method of claim 1, wherein the continuum light source is a mode-locked laser with nonlinear super continuum generating fiber.

4. The method of claim 1, wherein the light scattering apparatus comprises input light, at least one polarizing element, a scattering object, at least one output light polarizing element, and a detector.

5. The method of claim 1, wherein the detector is a charged coupled camera.

6. The method of claim 1, wherein the polarizers are crossed.

7. The method of claim 6, wherein the multiple order retarder is located between the crossed polarizers.

8. The method of claim 1, wherein the particular degree is 45 degrees.

9. The method of claim 1, wherein the apparatus is calibrated once during set up.

10. The method of claim 1, wherein variation in retardation over wavelength as opposed to variation in retardation with time is achievable with the photoelastic modulator or a variable modulator.

11. The method of claim 1, wherein the retarder is a broadband retarder that changes retardance slowly with wavelength.

12. The method of claim 1, wherein the retarder has one or more retardance cycles over the spectral range detected.

13. The method of claim 12, wherein the retarder is oriented at 45 degrees to a polarizer.

* * * * *